United States Patent [19]

Suzuki et al.

[11] Patent Number: 5,655,237
[45] Date of Patent: Aug. 12, 1997

[54] AIR CONTROLLED COMFORTER

[76] Inventors: Hiroko Suzuki; Emi Suzuki; Yoshio Suzuki, all of 11-32, Toneyama 6-chome, Toyonaka-shi, Osaka, Japan

[21] Appl. No.: 680,609

[22] Filed: Jul. 16, 1996

Related U.S. Application Data

[62] Division of Ser. No. 359,069, Dec. 19, 1994, Pat. No. 5,596,778.

[30] Foreign Application Priority Data

Dec. 20, 1993 [JP] Japan ..................... 5-345203

[51] Int. Cl.$^6$ ..................................... A47G 9/00
[52] U.S. Cl. .................. 5/502; 5/423; 607/107
[58] Field of Search ............... 5/941, 502, 423, 5/421, 284, 482; 607/107

[56] References Cited

U.S. PATENT DOCUMENTS

| | | | |
|---|---|---|---|
| 2,093,834 | 9/1937 | Gaugler | 5/423 |
| 2,601,189 | 6/1952 | Wales | 5/284 |
| 2,708,235 | 5/1955 | Kaplan | 5/502 |
| 2,711,546 | 6/1955 | Licht | 5/502 |
| 3,839,756 | 10/1974 | Hibbert | 5/502 |
| 3,951,127 | 4/1976 | Watson | 5/423 |
| 4,132,262 | 1/1979 | Wibell | 5/421 |
| 4,777,802 | 10/1988 | Feher | 5/423 |
| 5,300,100 | 4/1994 | Hickle | 5/423 |
| 5,324,320 | 6/1994 | Augustine | 5/482 |

FOREIGN PATENT DOCUMENTS

| | | | |
|---|---|---|---|
| 3235088 | 3/1984 | Germany | 5/502 |
| 149244 | 11/1931 | Switzerland | 5/423 |

*Primary Examiner*—Flemming Saether
*Attorney, Agent, or Firm*—Koda and Androlia

[57] ABSTRACT

In feather comforters and other comforters (primarily coverlet comforters) having a heat insulating material filled therein, to provide an air controlled comforter which makes it possible to obtain good sleep under comfortable sleeping conditions in terms of both temperature and humidity with the aid of warm or cool air, and which will not be moisturized itself so as to be free from the need of drying it each time after use. In a comforter in which a front cloth (1) and a rear cloth (2) is joined together at their peripheral edges to form a shape of bag, where a heat insulating material such as feather, wool, and cotton is filled in the bag, an air-permeable cloth (3) is joined with the rear cloth to define an air passage (4) ranging from hem to center part of the comforter. The air passage (4) is opened at the hem of the comforter, where an air opening (7) is provided for feeding warm or cool air. The warm or cool air fed through the opening to the air passage is passed through the sleeping space and the interior of the comforter with the heat insulating material filled therein, whereby a low-humidity, comfortable-temperature sleeping space is created while the comforter itself is dried.

2 Claims, 14 Drawing Sheets

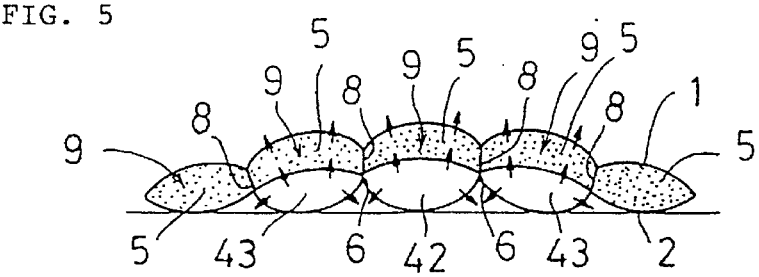
FIG. 5
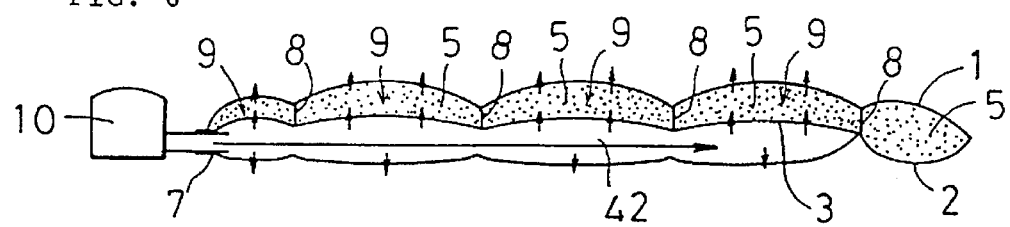
FIG. 6
FIG. 7
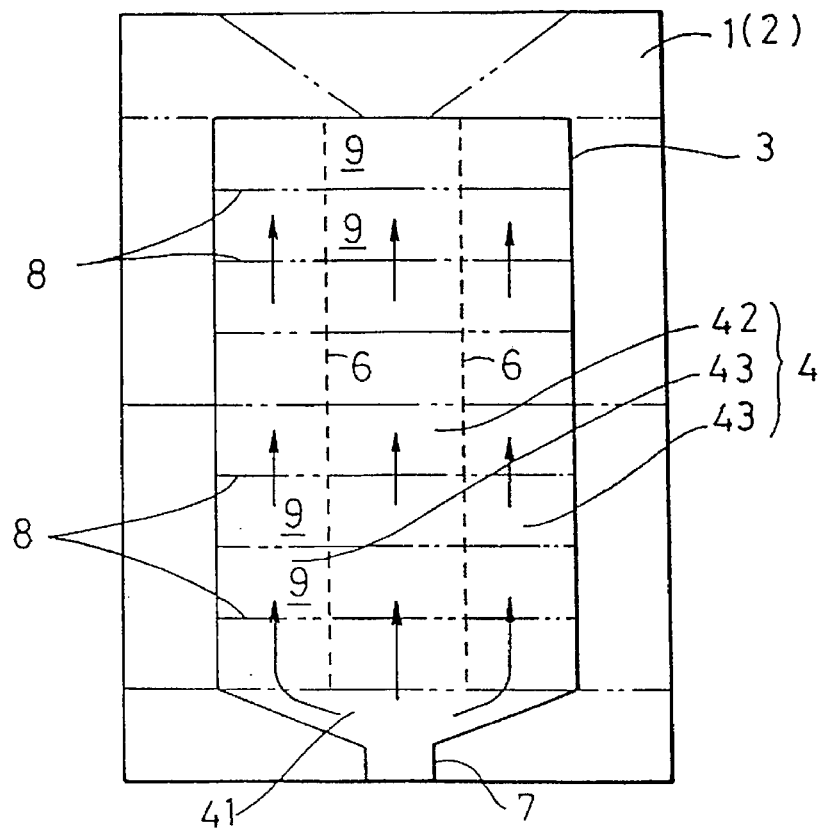

AIR CONTROLLED COMFORTER

This is a division of application Ser. No. 08/359,069, filed Dec. 19, 1994, now U.S. Pat. No. 5,596,778.

BACKGROUND OF THE INVENTION

1. Field of the Invention

The present invention relates to comforters in which a front cloth and a rear cloth are joined together at their peripheral edges into a shape of bag (on comforter side) and an interior wad such as feather, wool, and cotton (hereinafter, referred to as heat insulating material) is filled in the bag. More particularly, the invention relates to an air controlled comforter which can create a comfortable sleeping environment by feeding warm or cool air to the interior of the comforter.

2. Description of the Prior Art

Conventionally, there have been unavailable comforters that can be controlled in temperature or humidity. It has been usual practice in cold districts to use electric blankets, kotatsu, foot warmers, and the like. Known as the technique for warming a comforter itself with the aid of warm air are a concept of piping an air tube and a suction tube made of rubber tubes into the bed (Japanese Patent Publication SHO 40-16512), a concept of feeding warm air to an airtight bag-like body made of vinyl chloride resin or the like to effectuate heating (Japan Utility Model Publication SHO 43-21375, Japan Utility Model Publications SHO 43-21378 to -21380), and the like.

Conventional known comforters utilizing warm air are in all cases those designed for heating only, such that they could not be applied to coverlet comforters using a heat insulating material (wad). For example, comforters formed from a bag-like body of vinyl chloride resin have no moisture absorption property and could not afford to obtain a soft texture of coverlet comforters using a heat insulating material (wad) such as feather or wool. Further, since one discharges out a large amount of moisture (sweat) during sleep, increasing only the bed temperature would result in an overhumidity state in the bed due to the moisture discharged by himself or herself, so that he or she could not have a comfortable sleep.

SUMMARY OF THE INVENTION

According to the studies of the present inventors, it has been proved that the most comfortable sleeping conditions are a bed temperature of 31° C. and a humidity of 35 to 45%. In view of these circumstances, the present invention has come up with an air controlled comforter which utilizes warm or cool air and has a sleep-comforting heat insulating material filled therein, and which can implement optimum-temperature, low-humidity sleeping conditions.

The present invention provides an air controlled comforter in which a front cloth 1 and a rear cloth 2 are joined together at their peripheral edges by means of sewing or the like into a shape of bag, and a heat insulating material 5 such as feather, wool, and cotton is filled in the bag, the air controlled comforter characterized in that an air-permeable cloth 3 having air permeability is joined with the inner or outer surface of the rear cloth 2 constituting the comforter so as to form an air passage 4 on the rear of the comforter. The air passage 4 ranges from hem to center part of the comforter and is opened at the hem of the comforter, where an air opening 7 for feeding warm or cool air is provided at the opening.

The air passage 4 defined by the air-permeable cloth 3 may be such large sized as to cover the entire center part of the rear surface of the comforter, but it is preferably divided into such passages as will result in an appropriate air feed distribution of warm or cool air. For the purpose of this division, the air passage 4 may be branched from a foot-part air reservoir 41 communicating with the air opening into a center air passage 42 arranged in a center and side air passages 43, 43 arranged on its right and left sides. Also, the air passage 4 may be branched right and left so as to restrict the air feed to the center part of the comforter. Further, the air passage 4 may be formed so as to be detoured from peripheral side air passages 43 to inward intermediate air passages 44 by forming the intermediate air passages 44.

The present invention also provides an air controlled comforter comprising a front cloth 1 and a rear cloth 2, and two air-permeable cloths of a first air-permeable cloth 3a and a second air-permeable cloth 3b arranged between the front cloth and the rear cloth, wherein an air passage 4 ranging from hem to center part of the comforter is defined by joining together two air-permeable cloths of the first air-permeable cloth 3a and the second air-permeable cloth 3b; the front cloth 1 and the rear cloth 2, and the first air-permeable cloth 3a and the second air-permeable cloth 3b are joined together at their peripheral edges; and a heat insulating material 5 such as feather, wool, and cotton is filled in spaces between the front cloth 1 and the first air-permeable cloth 3a and between the second air-permeable cloth 3b and the rear cloth 2, whereby air passages are formed in the interior of the comforter.

As the air passages defined by the air-permeable cloth 3, one center air reservoir 45 or the side air passages 43 may be divided into thinner widths by joint line 11, 12. Also, at a shoulder part of the comforter, a shoulder comforter 13 independent of the comforter composed of the front cloth 1, the rear cloth 2, and the air-permeable cloth 3 may be fitted to an outer surface of the rear cloth 2.

As shown in FIGS. 1 to 3, warm or cool air is fed from the air opening 7 into the air passage 4 by a warm/cool air blower 10. Then the fed air passes through the rear cloth 2 and the air-permeable cloth 3 so as to be fed toward the sleeping space below or into the heat insulating material 5 as indicated by arrows, thus being diffused into the atmosphere. As a result, the sleeping space is heated or cooled to a proper temperature while the moisture in the sleeping space or the heat insulating material is evaporated so that an optimum humidity, for example a humidity of 35 to 40%, is maintained.

The air-permeable cloth 3 defining the air passage may be provided on either the outer surface or the inner surface of the rear cloth 2. Favorably, if the air-permeable cloth 3 is provided on the inner surface of the rear cloth 2, the rear cloth 2 will not be impaired in its soft feeling and appearance. Further, in a cubic quilt type feather comforter, if a cloth material impermeable to feather is used as the air-permeable cloth and if partition cloths 8 are provided between the front cloth 1 and the air-permeable cloth 3, then the functions as a cubic quilt type feather comforter will not be impaired.

If the air passage 4 ranging from hem to center part of the comforter is branched into the center air passage 42 and the right-and-left side air passages 43, 43, then the warm or cool air introduced into the air passage is fed uniformly over the entire range of the comforter. When the air passage is branched into the right-and-left side air passages 43, 43 or detoured from the side air passages 43 to the intermediate air passages 44, the warm air would be fed so as to cover the comforter from the surrounding, so that raw air will not impinge directly on the body, but that indirect heating or drying is effected. In the case where a small air-permeable portion 46 is provided between the side air passages and the center air reservoir, the warm or cool air is distributed in the bed less in the center part, where the comforter is applied to the body, so that the sleeper is less stimulated by the air.

In a comforter in which two air-permeable cloths of the upper air-permeable cloth 31 and the lower air-permeable cloth 32 form an air passage 4 inside the comforter, warm or cool air is fed necessarily through the heat insulating material into the bed. Also, in a comforter in which a shoulder comforter 13 is provided at the shoulder part of the comforter, the warm or cool air fed into the bed is inhibited from flowing up to the mouth of the sleeper through the spaces of the bed or the interior of the comforter.

When the warm or cool air is fed into the air passage, the air passage tends to swell like a tunnel. Therefore, a comforter in which one passage is divided into partitions with thin widths by joint lines is limited in the magnitude of swell due to the fed air so that the whole comforter will not swell more than needed.

BRIEF DESCRIPTION OF THE DRAWINGS

FIG. 5 is a center lateral sectional view of the embodiment shown in FIG. 4;

FIG. 6 is a center longitudinal sectional view of the embodiment shown in FIG. 4;

FIG. 7 is a plan view showing an embodiment in which the second embodiment is applied to a feather comforter of the bodily-shape cubic quilt type shown in FIG. 4;

DETAILED DESCRIPTION OF THE PREFERRED EMBODIMENTS

Now embodiments of the air controlled comforter of the present invention are described with reference to the accompanying drawings.

Figure 1:
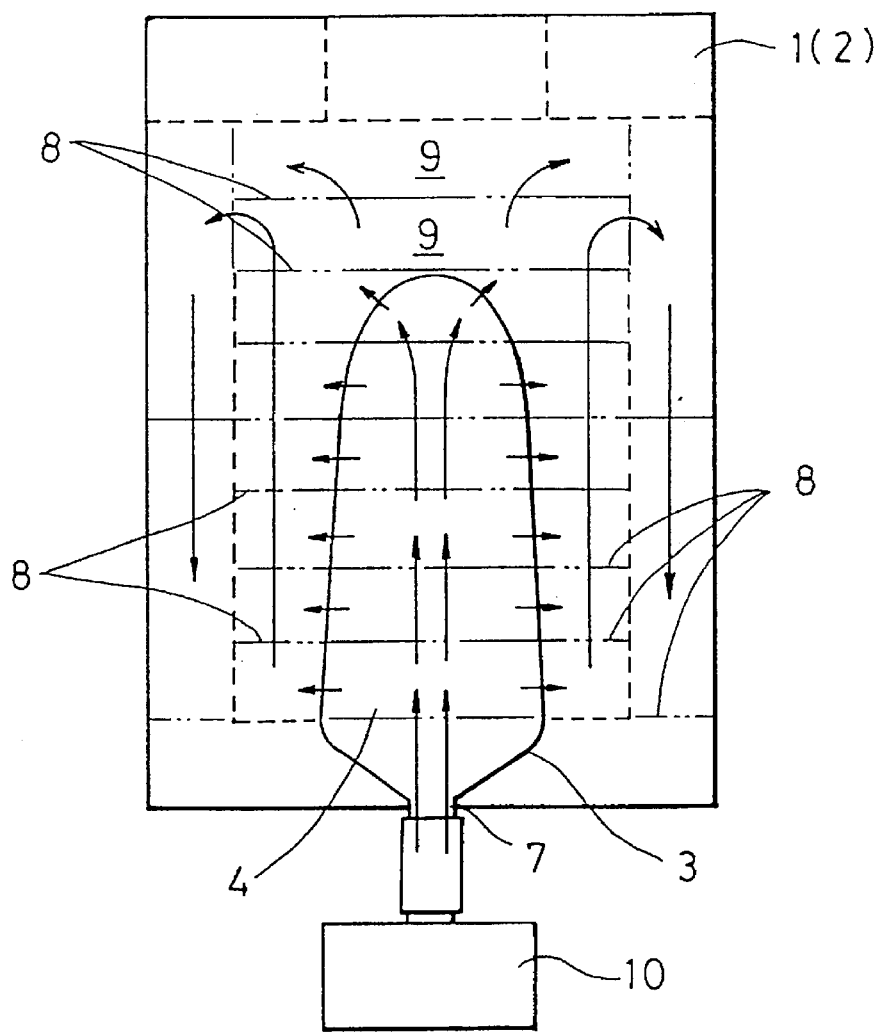
FIG. 1 is a plan view showing a first embodiment of the present invention.
Figure 2:
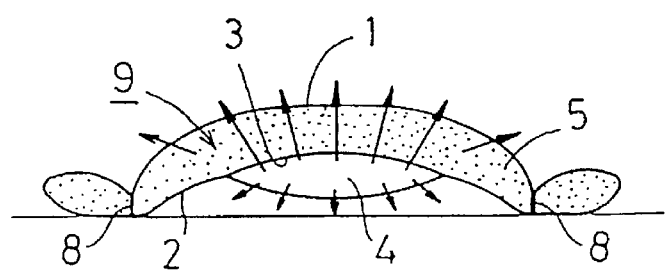
FIG. 2 is a center lateral sectional view of the embodiment shown in FIG. 1.
Figure 3:
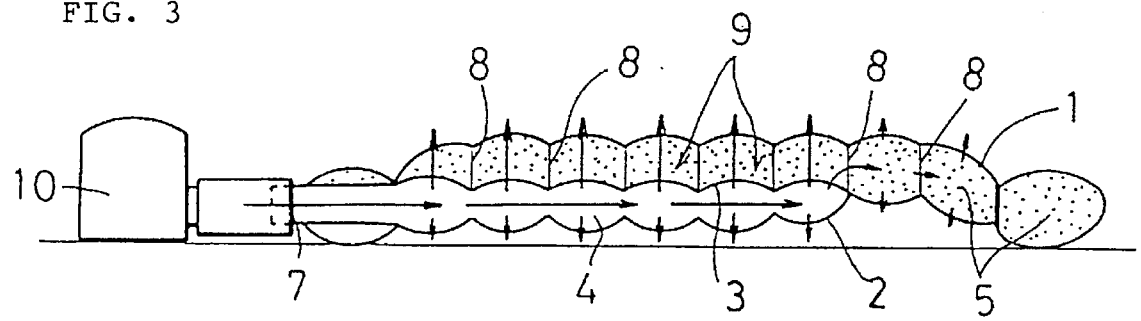
FIG. 3 is a center longitudinal sectional view of the embodiment shown in FIG. 1.

FIGS. 1 to 3 show an embodiment in which the present invention is applied to a cubic quilt type feather comforter. In a comforter composed of a front cloth 1 and a rear cloth 2, an air-permeable cloth 3 is joined with the rear cloth 2 to define an air passage 4. In the figures, the air passage 4 defined by the air-permeable cloth 3 is indicated by solid line, partition cloths 8 constituting the cubic quilt are indicated by two-dot chain line, and partition cloths made from a cloth material having poor gas-permeability out of the partition cloths are indicated by broken line.

In this embodiment, as shown in FIGS. 2 and 3, the air-permeable cloth 3 that is tongue shaped in its plan view and that ranges from hem to center part of the comforter is sewn on the inner surface of the rear cloth 2, so that an air passage 4 is formed between the rear cloth 2 and the air-permeable cloth 3, with an air opening 7 opened at the hem of the comforter. Thus it is arranged that warm air and cool air can be fed into the air passage 4 by a warm/cool air blower 10 through the air opening 7. The air to be fed to the air passage 4 will be warm air in winter for heating and dehumidifying the comforter interior and the sleeping space, or cool air (normal temperature) in summer primarily for dehumidifying. Hereinbelow, both types of air are generically referred to simply as "warm air".

The warm air fed to the air passage 4 moves downward (to sleeping space) and inward of the comforter having a heat insulating material filled therein, as shown in FIGS. 1 to 3. Thus, the air acts to warm the sleeping space and the interior of the comforter and moreover to evaporate the moisture emitted from the body, thereby controlling the sleeping space and the comforter interior to proper temperature and humidity. The warm air that has moved to the interior of the comforter, although partly discharged into the atmosphere immediately, partly moves inward of the comforter, thereby exerting the functions of heating and drying the whole comforter. In the embodiment as shown in FIG. 1, partition cloths having poor air-permeability are used in the interior of the comforter as indicated by broken line, so as to define an air passage for the warm air in the comforter. Thus, it is arranged that the fed warm air will circulate from center to peripheral part of the comforter. For this circulation of the warm air, it is devised that the warm air will be fed to the compartments of the shoulder part (top in the figure) close to the chest or face as less as possible, so that heated or dried air will not cause a stuffy or thirsty sleep.

Figure 4:
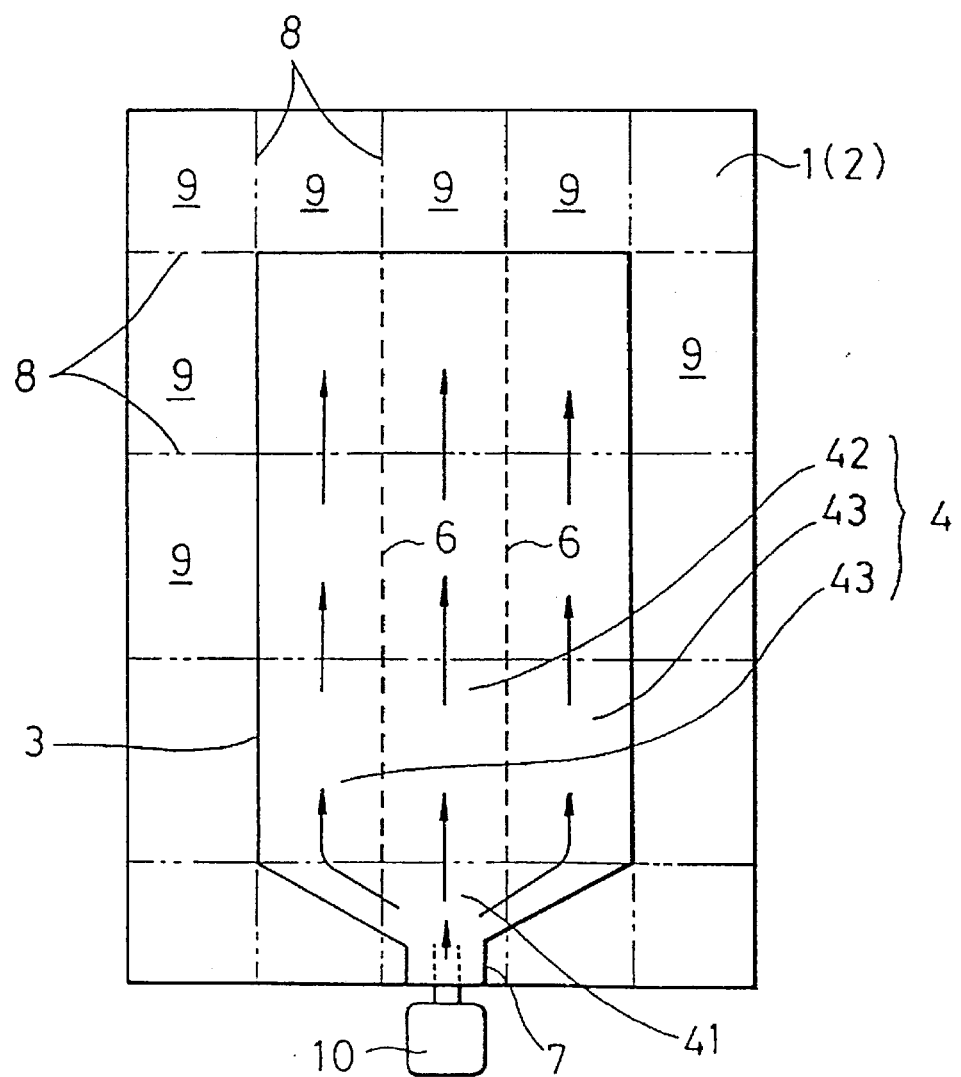
FIG. 4 is a plan view showing a second embodiment of the present invention.

An embodiment of the present invention as shown in FIGS. 4 to 5 is so arranged that the air passage 4 is divided into a center air passage 42 and side air passages 43, 43 by joint lines 6, 6, whereby the warm air fed from the air opening 7 to the air passage will be fed from the foot-part air reservoir 41 to the center air passage 42 and the two side air passages 43, 43. In this embodiment, therefore, the warm air will be fed over the entire center part of the comforter, more uniformly.

The partition cloths 8 in the cubic quilt type feather comforter are generally arranged into a longitudinal and lateral lattice shape, which is so called European quilt. However, the present inventors have invented a quilt in which partition cloths are relatively thin in width and extended in the widthwise direction so that the feather distribution is naturally matched to the bodily shape (referred to as a bodily-shape cubic quilt), and a quilt in which the partition cloths are shaped into a down slope outwardly and a swell in their center part (referred to as a cubic dome quilt). The present invention is applicable to these various types of quilt feather comforters as well as general cotton comforters and wool comforters. The embodiment as shown in FIGS. 1 to 3 and FIG. 7 is a case where the present invention is applied to the bodily-shape cubic dome quilt. The embodiment as shown in FIGS. 4 to 6 is a case where the present invention is applied to the cubic dome quilt of European quilt.

Although the air-permeable cloth 3 may be sewn on the outer surface of the rear cloth 2, it results in a better appearance when sewn on the inner surface of the rear cloth 2. Accordingly, in the embodiment in which the air-permeable cloth 3 is sewn on the inner surface of the rear cloth 2 and the comforter is a feather comforter of the cubic quilt type, the partition cloths 8 within the range over which the air-permeable cloths are present are formed between the front cloth 1 and the air-permeable cloth 3, where feather is filled in their compartments 9 as a heat insulating material 5.

Figure 8:
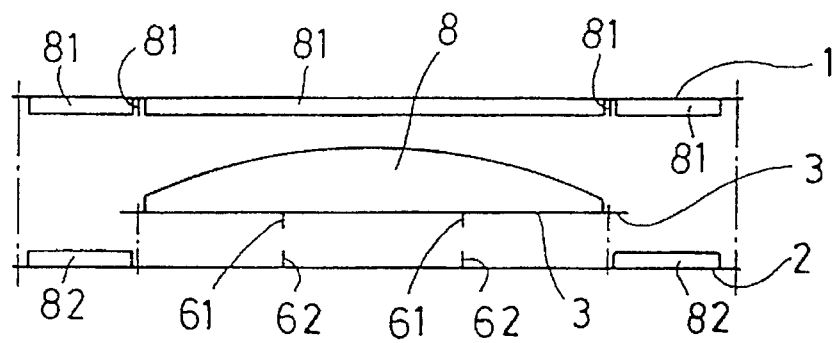
FIG. 8 is an exploded sectional view of the embodiment shown in FIG. 7.

FIG. 8 is an exploded sectional view of the embodiment as shown in FIG. 7. To describe its manufacturing process with reference to FIG. 8, previously sewn is a front-cloth docking tape 81 that will form part of the partition cloths of the cubic quilt and that will be sewn with the partition cloths 8 or a rear-cloth docking tape 82. Also previously sewn are air-passage dividing docking tapes 61, 61 for forming the partition cloths 8 on the upper surface of the air-permeable cloth 3 and the joint lines 6 on the lower surface of the air-permeable cloth 3. On the inner surface of the rear cloth 2, also previously sewn are the rear-cloth docking tapes 82, 82 that will form part of the partition cloths, and air-passage dividing docking tapes 62, 62 for forming the joint lines 6.

First, the air-passage dividing docking tape 61 of the air-permeable cloth 3 and the air-passage dividing docking tape 62 of the rear cloth 2 are sewn together, and both of them are integrated together by sewing peripheral portions of the air-permeable cloth 3 with specified portions of the rear cloth 2. Subsequently, compartments 9 are formed between the front cloth 1 and the rear cloth 2 or the air-permeable cloth 3 by sewing together the front-cloth docking tapes 81, 81 and the partition cloth 8 and the rear-cloth docking tape 82. In this process, the peripheral portions of the air-permeable cloth 3 can be utilized as part of the docking tape. It is noted that clearances for filling feather into the compartments 9 are left for the process of sewing the partition cloth. Finally, peripheral edges of the front cloth 1 and the rear cloth 2 are sewed together, and feather is filled into the compartments. Thus, the air controlled comforter of FIG. 7 is completed.

FIGS. 9 to 13 show an embodiment having two-system air passages formed, a case where the present invention is applied to a feather comforter of bodily-shape dome quilt. This embodiment is so arranged that a minimum of warm air will be fed to the center part of the comforter, which part is to be applied directly onto the body of the sleeper. More specifically, the comforter comprises two-system air passages, a first air passage 4a communicating with a first air opening 7a and a second air passage 4b communicating with a second air opening 7b, wherein the first air passage 4a communicating with the first air opening 7a is branched from a first foot-part air reservoir 41a toward right-and-left sides of the center part. The second air passage 4b communicating with the second air opening 7b is formed into generally U shape from a second foot-part air reservoir 41b along the outer periphery of the first air passage 4a. The first foot-part air reservoir 41a, which occupies a somewhat large area, is provided with support cloths 14, 14 made from a cloth material having such high permeability as will not make a resistance against air flow, in order that the portion of the first foot-part air reservoir 41a will not be swollen.

Figure 9:
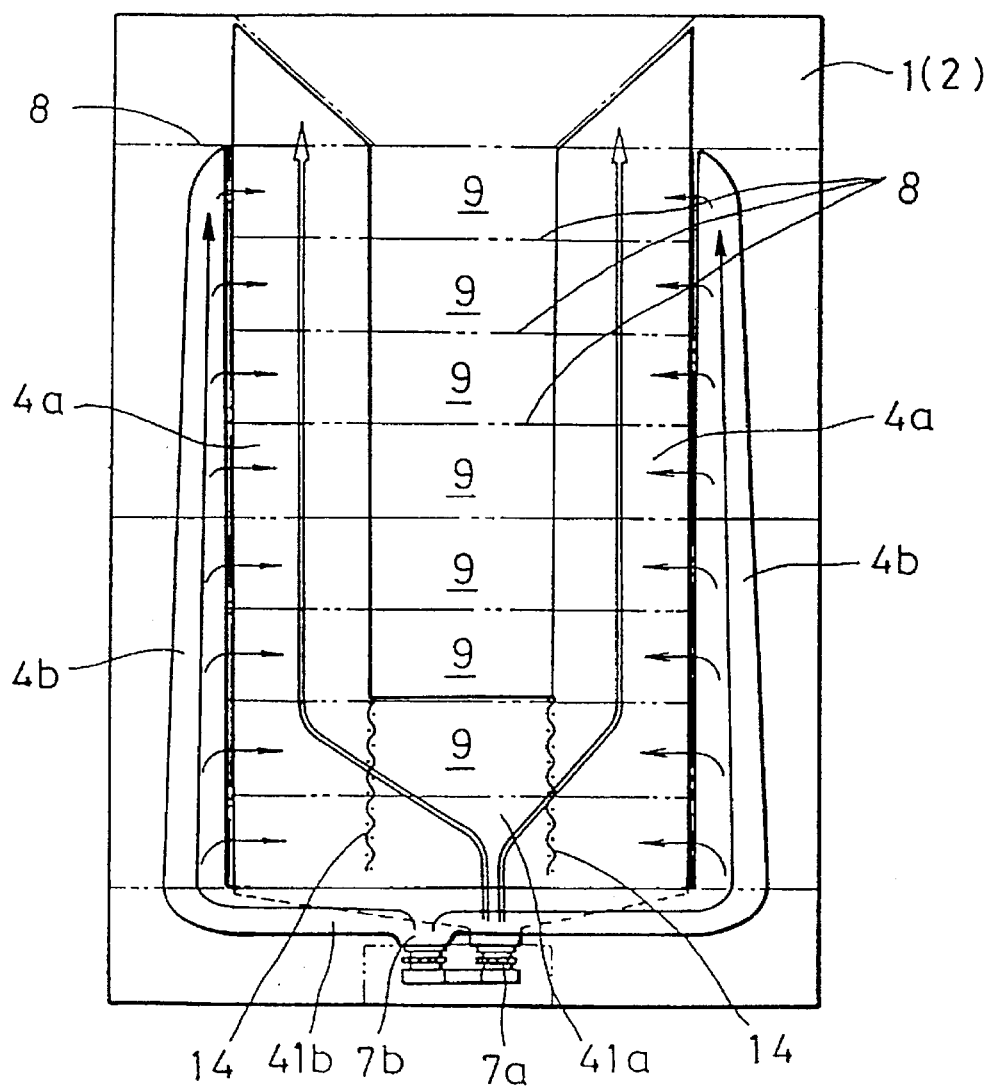
FIG. 9 is a plan view showing a third embodiment of the present invention.
Figure 10:
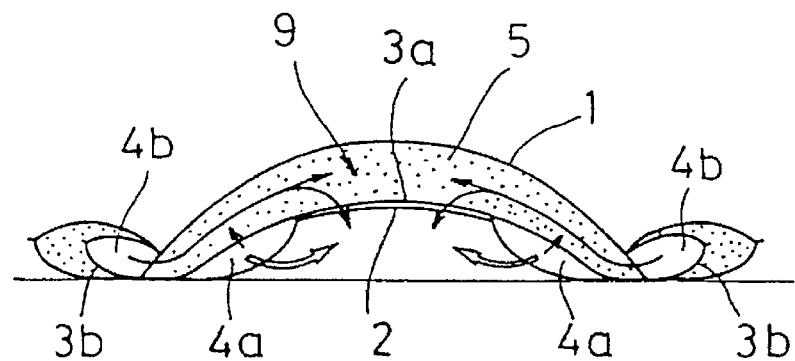
FIG. 10 is a center lateral sectional view of the embodiment shown in FIG. 9.

As shown in FIGS. 9 and 10, warm air fed to the first air passage 4a is fed directly to the air passages branched to the right and left sides of the center part of the comforter, as indicated by unshaded arrows. To the sleeping space, most warm air is fed sideways of the body of the sleeper through the rear cloth 2 corresponding to the first air passage 4a portion, while some of the warm air is introduced into the compartments 9 inside the comforter by being passed through the first air-permeable cloth 3a of the first air passage. This warm air serves to heat and dry the heat insulating material in the comforter, and part of the warm air is fed indirectly to the sleeping space from above the center part of the comforter. Meanwhile, the warm air fed to the second air passage 4b acts to gradually heat the sleeping space and the interior of the comforter while passing through the interior of the comforter from its peripheral portions, as indicated by black arrows. Accordingly, in this embodiment, the comforter can be used in such a way that the comforter is heated promptly to preferable sleeping conditions by feeding air from the first air passage immediately before and after the sleeper goes to bed, and that warm air is fed gradually from the second air passage in a gentle, less stimulative state after the sleeper has gone to sleep. Thus, the comforter can realize a stable sleeping environment.

The air passage of the air controlled comforter as shown in FIG. 9 can be made by sewing the first air-permeable cloth 3a for defining the first air passage and the second air-permeable cloth 3b for defining the second air passage to the rear cloth 2.

Figure 11:
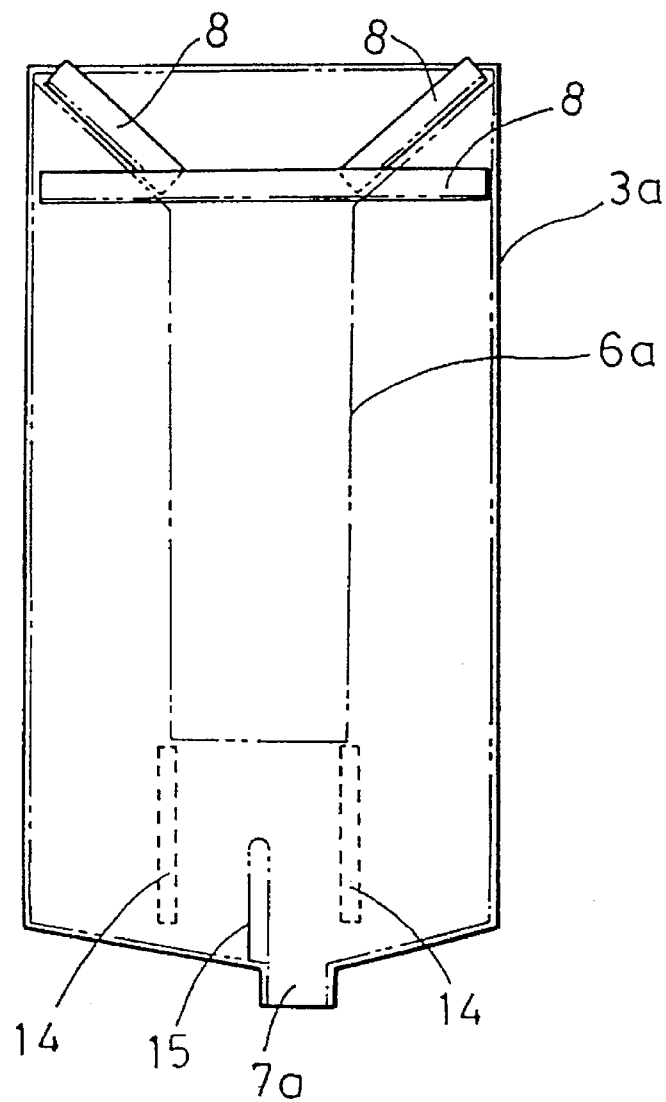
FIG. 11 is a plan view of the first air-permeable cloth of the embodiment shown in FIG. 9.

FIG. 11 shows a plan view of the first air-permeable cloth 3a. The comforter is made from a cloth material that is permeable to air but impermeable to feather, and formed into a generally rectangle of such a size as to cover the whole center part of the comforter, where the first air opening 7a is provided at the hem. Partition cloths 8, 8 (center-part partition cloths are omitted in the figure) are sewn on the upper surface of the first air-permeable cloth 3a, while support cloths 14, 14 are sewn on the lower surface. In FIG. 11, a first air-permeable cloth joint line 6a is indicated by two-dot chain line. As understood from the shape of this first air-permeable cloth joint line 6a, the air passage defined by sewing the rear cloth 2 and the first air-permeable cloth 3a together is branched to right and left sides.

Otherwise, in the embodiment as shown in the figure, a sensor bag 15 for incorporating a control-use sensor is sewn on the first air-permeable cloth 3a.

Figure 12:
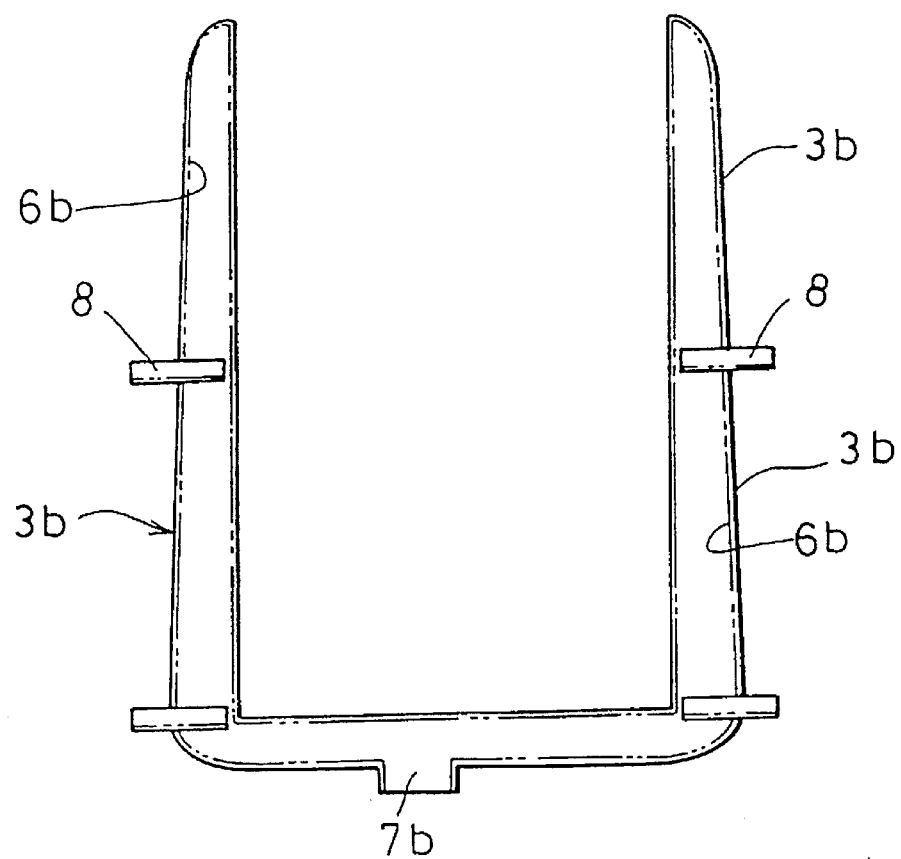
FIG. 12 is a plan view of the second air-permeable cloth of the embodiment shown in FIG. 9.

FIG. 12 is a plan view of the second air-permeable cloth 3b, which as a whole is shaped into a generally U shape of a size along the outer periphery of the first air-permeable cloth 3a, in an upper-and-lower double structure. Out of the entire periphery of the second air-permeable cloth 3b, the peripheral edge other than abutting to the first air-permeable cloth is sewn along a second air-permeable cloth joint line 6b indicated by two-dot chain line. Also, partition cloths 8, 8 each located at a side portion of the comforter are sewn on the upper cloth and the lower cloth of the second air-permeable cloth 3b of upper-and-lower double structure, while a second air opening 7b is provided at the hem. This second air-permeable cloth 3b is arranged along the outer periphery of the first air-permeable cloth 3a, and its inner periphery abutting the first air-permeable cloth 3a is sewn on the rear cloth together with the first air-permeable cloth.

Figure 13:
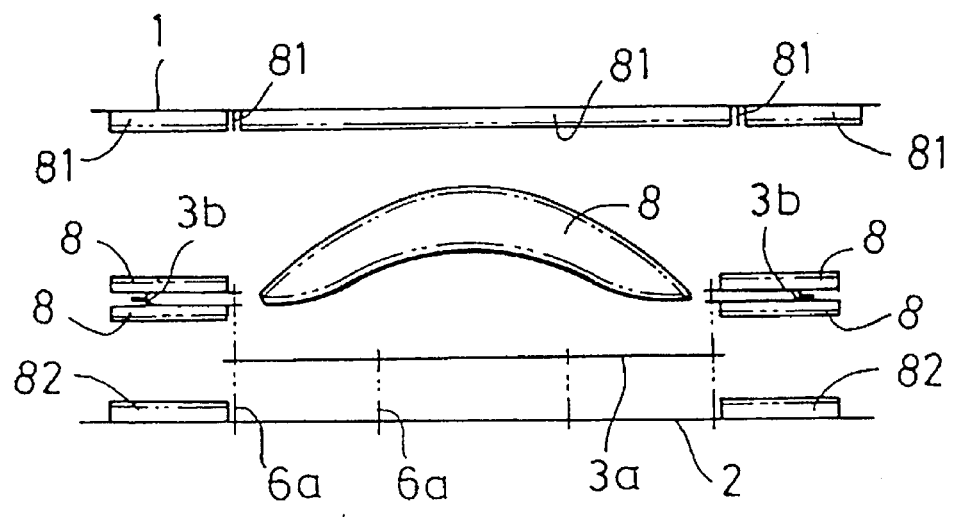
FIG. 13 is an exploded sectional view of the embodiment shown in FIG. 9.

FIG. 13 is an exploded sectional view of the embodiment shown in FIG. 9. The manufacturing process therefor is now described with reference to FIG. 13. On the lower surface of the front cloth 1, a front-cloth docking tape 81 is sewn that will form part of the partition cloth of the cubic quilt and that will be sewn with the partition cloths 8. Previously, partition cloths 8, 8 of the center part of the comforter are sewn on the upper surface of the first air-permeable cloth 3a, partition cloths 8, 8 located at side portions of the comforter are sewn on the upper and lower cloths of the second air-permeable cloth 3b, and the rear-cloth docking tape 82 of the partition cloth located at side portions of the comforter is sewn on the upper surface of the rear cloth 2. In this state, the first air-permeable cloth 3a and the rear cloth 2 are sewn along the first air-permeable cloth joint line 6a of FIG. 11. More specifically, at the portion abutting the second air-permeable cloth, the first air-permeable cloth 3a and the second air-permeable cloth 3b together are sewn on the rear cloth 2, so that the three of the first air-permeable cloth 3a, the second air-permeable cloth 3b, and the rear cloth 2 are integrated together. In this process, the partition cloths 8 of the second air-permeable cloth 3b and the rear-cloth docking tape 82 are sewn. Subsequently, the partition cloths 8 of the first air-permeable cloth 3a and the second air-permeable cloth 3b, and the front-cloth docking tapes 81 of the front cloth 1 are sewn together, so that the partition cloths in the comforter are completely made up. Moreover, peripheral edges of the front cloth 1 and the rear cloth 2 are sewn together, and feather is filled in the compartments 9 defined by the partition cloths. Thus, the feather comforter having a sectional structure as shown in FIG. 10 is completely made up.

Figure 14:
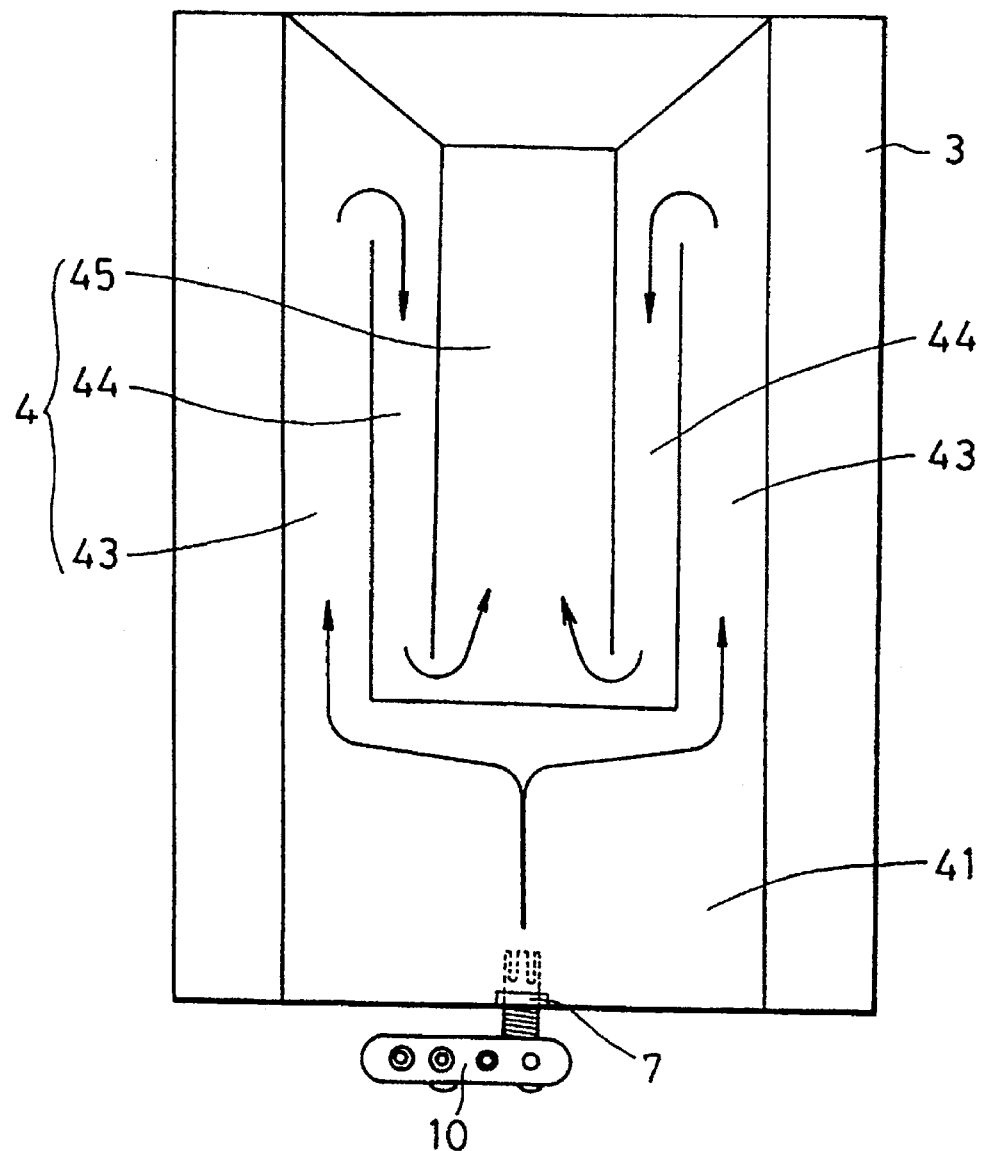
FIG. 14 is a plan view showing a fourth embodiment of the present invention.
Figure 15:
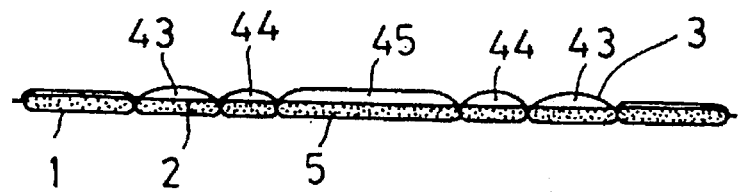
FIG. 15 is a center lateral sectional view of the embodiment shown in FIG. 14.
Figure 16:
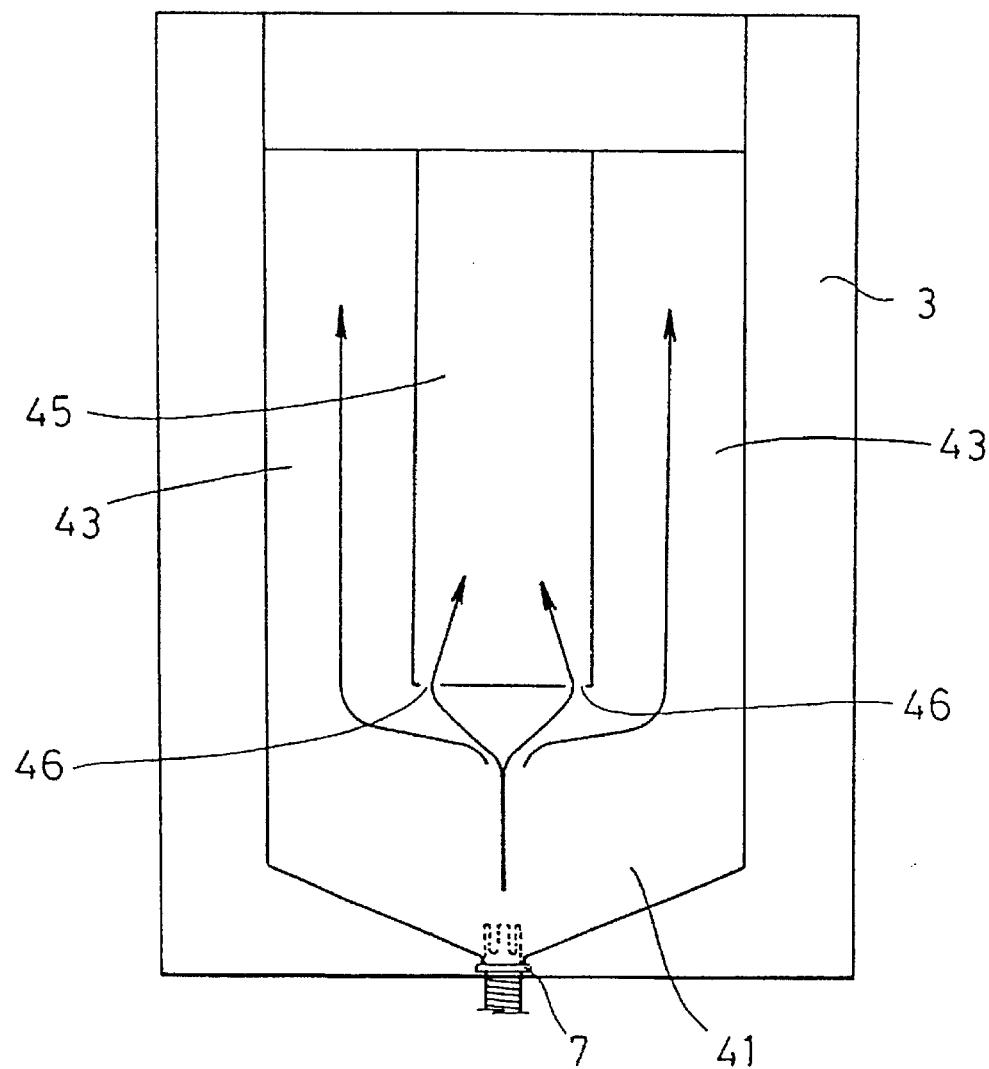
FIG. 16 is a plan view showing a fifth embodiment of the present invention.

FIGS. 14 to 16 show embodiments in which the air-permeable cloth 3 is arranged so as to overlap with a thin comforter rear cloth 2, and the comforter including the front cloth 1 and the rear cloth 2 is directly sewn up as a whole, thus making up an air-controlled type comforter. In these embodiments, an air passage 4 may be formed optionally, depending on sewing lines. In the embodiment as shown in FIG. 14, warm air introduced from the air opening 7 to the foot-part air reservoir 41 moves through the side air passage 43 to the chest part. Then, the air detours inward and passes through the intermediate air passage 44, thus reaching the center air reservoir 45 arranged in the center part of the comforter. In this embodiment, the air is blown off into the sleeping space primarily sideways of the sleeper's body.

In the embodiment as shown in FIG. 16, warm air introduced from the air opening 7 to the foot-part air reservoir 41 of the air passage is branched into the right-and-left side air passages 43, 43. Besides, the air is fed to the center air reservoir 45 through small air-permeable portions 46, 46 formed by omitting the sewing line of the air-permeable cloths. Since the flow rate of the warm air introduced depends on the size of the air-permeable portions 46, it is recommendable to determine the size of the air-permeable portions 46 so that such warm air as will not stimulate the body and as can realize a preferable sleeping environment can be fed to the center air reservoir 45. The comforters as shown in FIGS. 14 to 16 are ones that can be manufactured most simply, and that make it possible to provide an air controlled comforter with relatively low price.

Figure 17:
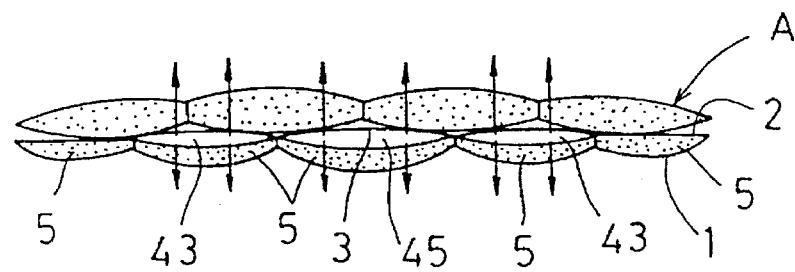
FIG. 17 is a center lateral sectional view showing an example of the state in which the comforter of the embodiment shown in FIG. 16 is used.

The comforters as shown in FIGS. 14 to 16 may be used either singly by themselves or in combination with an ordinary comforter. More specifically, the comforter, when used singly, is positioned with the surface of the air-permeable cloth 3 down. However, when the comforter is used in combination with another comforter, it is used upside down as shown in FIG. 17, with the surface of the air-permeable cloth 3 up and with an ordinary comforter A overlapped thereon. In this case, the warm air introduced into the air passage 4 is fed to the sleeping space by passing through the front cloth 1 and the rear cloth 2 of the comforter as indicated by arrows. Meanwhile, the warm air that has passed through the air-permeable cloth 3 passes through the comforter A, thus being discharged into the atmosphere. In this process, the warm air acts to heat and dry the comforter A. The warm air fed to the sleeping space is indirect air that has passed through the heat insulating material of the comforter. As a result, a less-stimulative, soft sleeping environment is created.

Figure 18:
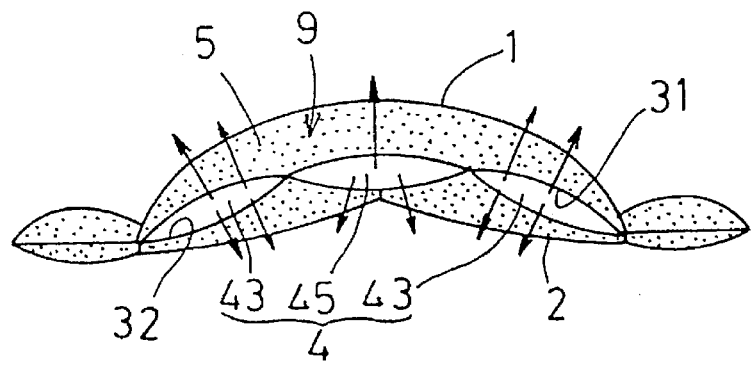
FIG. 18 is a center lateral sectional view showing a sixth embodiment of the present invention.
Figure 19:
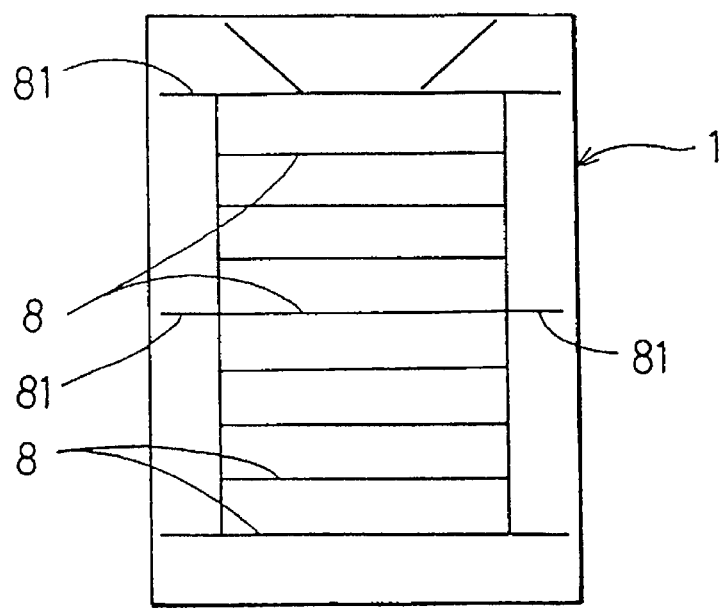
FIG. 19 is a plan view of the front cloth of the embodiment shown in FIG. 18 as viewed from the rear suface.
Figure 20:
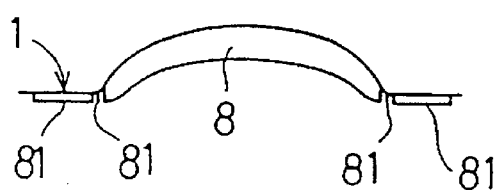
FIG. 20 is a front view of the front cloth of the embodiment shown in FIG. 18.
Figure 21:
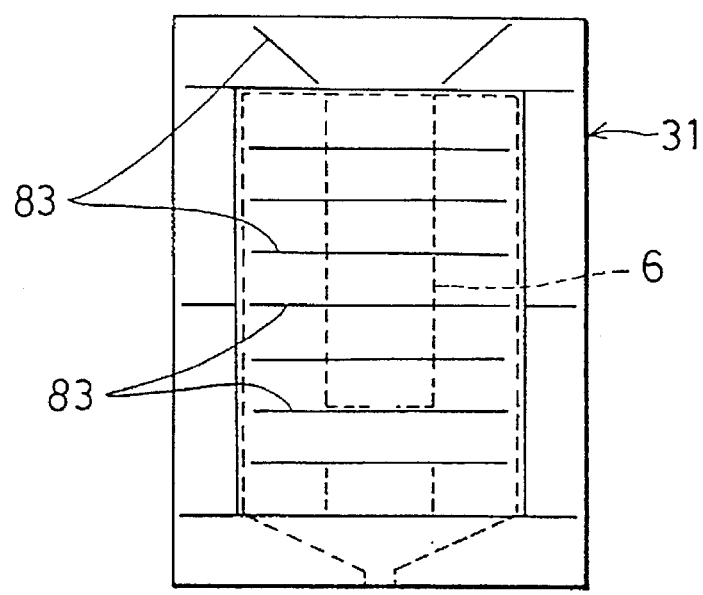
FIG. 21 is a plan view of the upper air-permeable cloth of the embodiment shown in FIG. 18.
Figure 22:
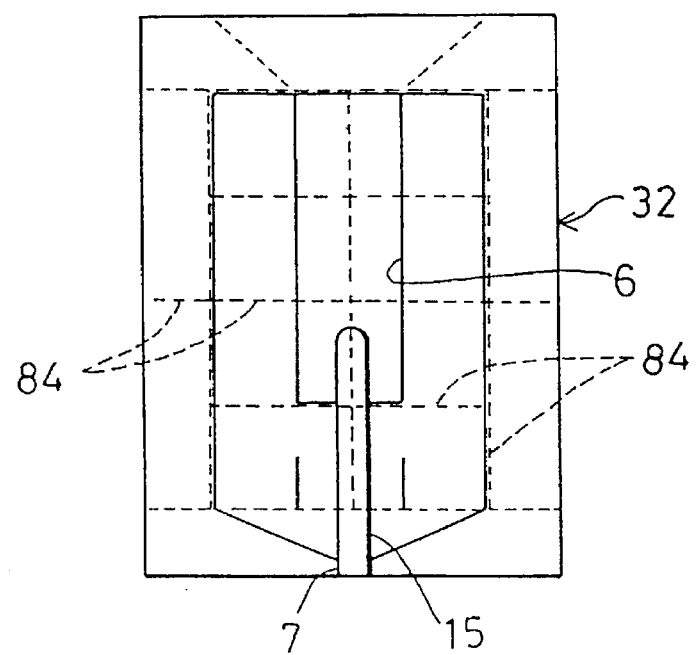
FIG. 22 is a plan view of the lower air-permeable cloth of the embodiment shown in FIG. 18.
Figure 23:
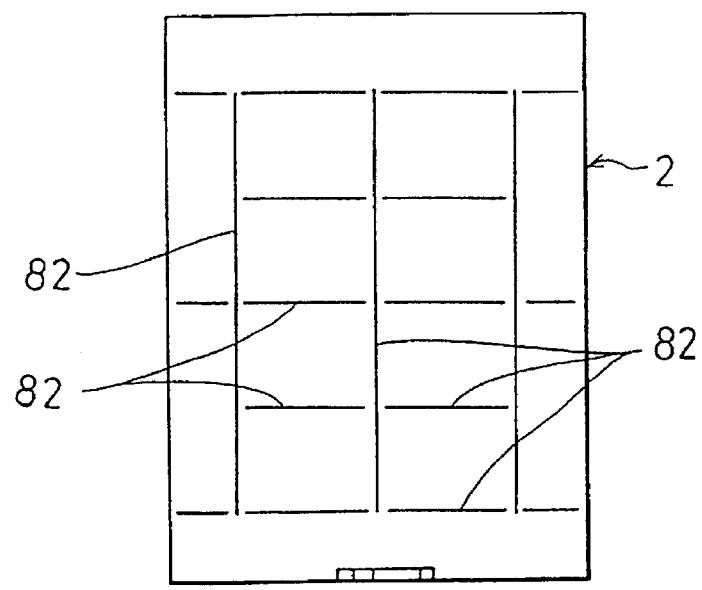
FIG. 23 is a plan view of the rear cloth of the embodiment shown in FIG. 18.
Figure 24:
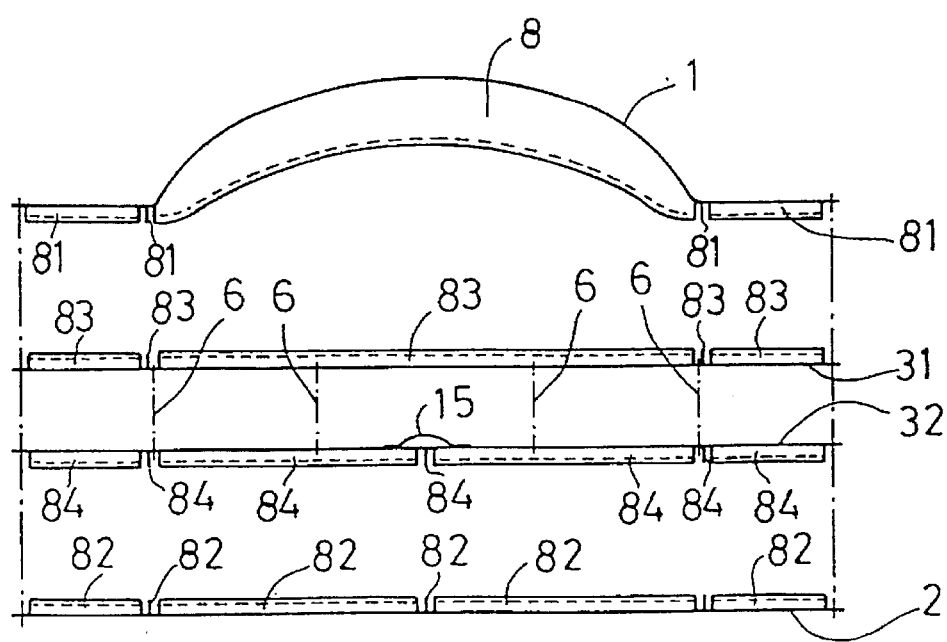
FIG. 24 is an exploded sectional view of the embodiment shown in FIG. 18.

FIGS. 18 to 24 show an embodiment in which the air passage 4 for warm or cool air is formed inside the comforter, and warm air to be fed is normally discharged into the sleeping space or the atmosphere by passing through either an upper or a lower heat insulating material, that is, the comforter is arranged normally into the state as shown in FIG. 17. The air controlled comforter according to this embodiment comprises totally four sheets of cloth material, a front cloth 1 as shown in FIGS. 19 and 20, an upper air-permeable cloth 31 as shown in FIG. 21 and a lower air-permeable cloth 32 as shown in FIG. 22, and a rear cloth 2 as shown in FIG. 23. That is, the air passage 4 is formed in the interior of the comforter, by joining together the upper air-permeable cloth 31 and the lower air-permeable cloth 32 into a specified state between the front cloth 1 and the rear cloth 2. In the embodiment shown in the figures, the air passage 4 is divided into side air passages 43, 43 and a center air reservoir 45. The four cloths of the front cloth 1, the rear cloth 2, the upper air-permeable cloth 31, and the lower air-permeable cloth 32, which constitute the comforter, are all made from a cloth material having air-permeability and a texture of feather-impermeability. FIG. 24 is an exploded sectional view of the embodiment shown in FIG. 18. Its manufacturing process is now described with reference to FIGS. 19 to 24.

As shown in FIGS. 19 and 20, one side edge of the partition cloths 8 of the cubic quilt and the front-cloth docking tapes 81 are sewn on the lower surface of the front cloth 1 in a specified arrangement (cubic type dome quilt in the embodiment of the figure). Also, as shown by solid line in FIG. 21, on the upper surface of the upper air-permeable cloth 31, upper air-permeable cloth docking tapes 83, 83 are sewn at locations corresponding to the partition cloths 8 of the front cloth 1 and the front-cloth docking tapes 81. Besides, as shown by broken line in FIG. 22, on the lower surface of the lower air-permeable cloth 32, one side edge of lower air-permeable docking tapes 84, 84 is sewn in a specified arrangement (European quilt with the center part of the comforter lattice-shaped in the figure). The upper air-permeable cloth 31 and the lower air-permeable cloth 32 are joined together along joint lines 6, thereby defining the air passage 4 of a desired shape. The joint lines 6 are indicated by broken lines in FIG. 21 and by solid line in FIG. 22. The air passage as shown in this embodiment is branched both right and left from the air opening 7. It is noted that a sensor bag 15 ranging from the air opening 7 nearly to the center part of the comforter is sewn on the upper surface of the lower air-permeable cloth 32.

On the upper (inner) surface of the rear cloth 2, as shown by solid line in FIG. 23, one side edge of the rear-cloth docking tape 82 is sewn in correspondence to the positions of the lower air-permeable docking tapes 84, 84 sewn to the lower air-permeable cloth 32.

As shown in FIG. 24, the upper air-permeable cloth 31 and the lower air-permeable cloth 32 are sewn by the joint lines 6 so as to define the air passage 4. Subsequently, the partition cloths 8 and the front-cloth docking tapes 81 sewn to the front cloth 1 are sewn together with the upper air-permeable cloth docking tapes 83, 83 sewn to the upper air-permeable cloth 31. Besides, the lower air-permeable docking tapes 84, 84 sewn to the lower air-permeable cloth 32 are the rear-cloth docking tapes 82, 82 sewn to the upper air-permeable cloth 31 are sewn together. Finally, the four cloths of the front cloth 1, the upper air-permeable cloth 31, the lower air-permeable cloth 32, and the rear cloth 2 are sewn together, and feather is filled into the compartments between the front cloth 1 and the upper air-permeable cloth 31 and between the lower air-permeable cloth 32 and the rear cloth 2. Thus, an air controlled comforter having an air passage defined inside the comforter as shown in FIG. 18 is completed.

In this embodiment shown in the figure, the comforter is so arranged that a bodily-shape cubic dome quilt is formed above the air passage 4 while a lattice-shaped cubic quilt is formed below the air passage. However, the comforter may be such a feather comforter, as well as a cotton comforter or a wool comforter that a bodily-shape quilt or a lattice-shaped quilt of the same formation is formed both above and below the air passage. In brief, it is only required for the comforter that a space in which a heat insulating material is filled between the front cloth and the upper air-permeable cloth and between the lower air-permeable cloth and the rear cloth, and that the air passage 4 is formed between the upper air-permeable cloth 31 and the lower air-permeable cloth 32.

As a result of the studies of the present inventors, it has been recognized that with a 20° C. room temperature, when 28° C. warm air is continuously fed to the air passage 4, the sleeping space is stabilized in ideal conditions of a temperature around 31° C. and a humidity of around 35% from the relation with the sleeper's temperature. However, it has also been proved that the sleeper may feel thirsty and dry during the sleep due to the dry air filled around the sleeper's head.

Figure 25:
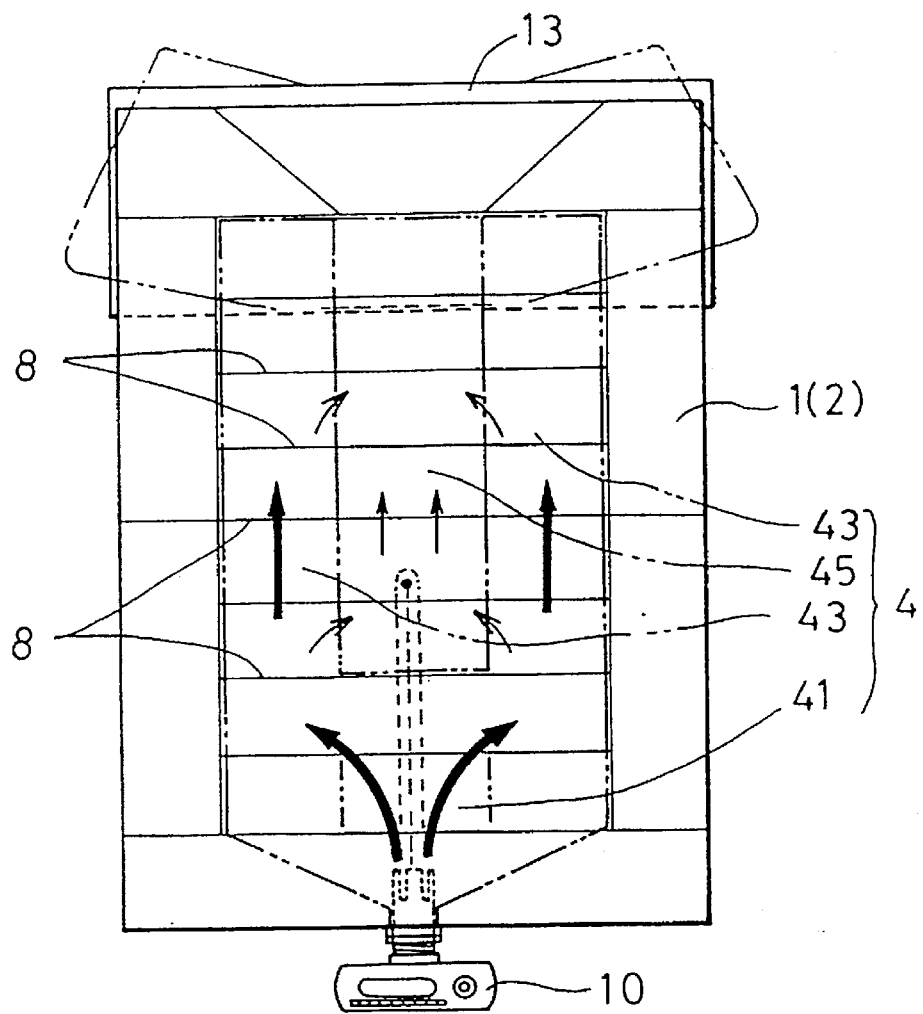
FIG. 25 is a plan view showing a seventh embodiment of the present invention in which a shoulder comforter is fitted.
Figure 26:
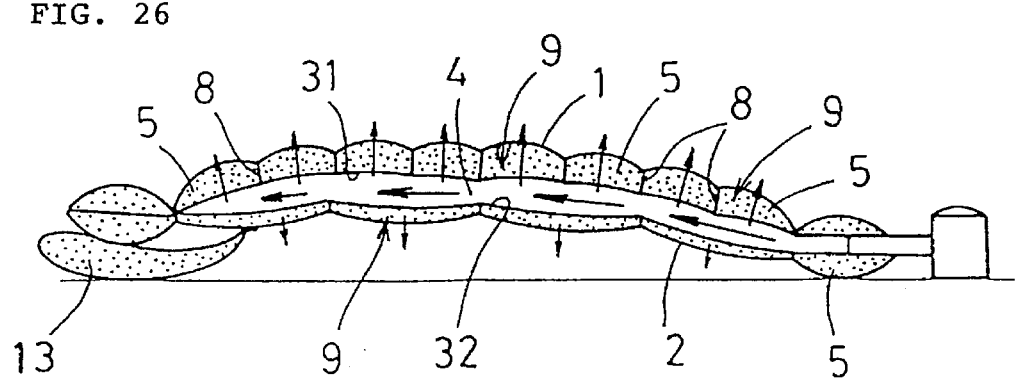
FIG. 26 is a center longitudinal sectional view of the embodiment shown in FIG. 25.

To solve this problem, embodiments as shown in FIGS. 25 and 26 are so arranged that a shoulder comforter 13 which is independent of the comforter made up of the front cloth 1, the rear cloth 2, and the air-permeable cloth and which comprises an upper comforter alone is sewn to the outer surface of the rear cloth 2 at the shoulder part opposite to the hem of the comforter, so that the shoulder comforter 13 covers the chest and shoulder parts of the sleeper. As a result, the warm air thrown into the comforter interior will not be filled around the sleeper's head. Thus, the problems of the dry and thirsty feelings during sleep have been solved.

The shoulder comforter 13 of the embodiments as shown in FIGS. 25 and 26 may be one sewn to the rear cloth 2 over the entire widthwise length, but is desirably sewn at a center part in the widthwise direction. This arrangement makes it possible to use the shoulder comforter 13 as it is shifted upward by both right and left sides, as shown by two-dot chain line in FIG. 25, so that the shoulder part that is likely to be cooled during sleep can be covered from around.

When warm air is fed to the air passage, the air passage 4 tends to swell like a tunnel by its internal pressure even if the air-permeable cloth has air-permeability. In this connection, if the air passage is large sized, it is likely that the whole comforter may swell too much so as to be rounded, becoming difficult to use.

Figure 27:
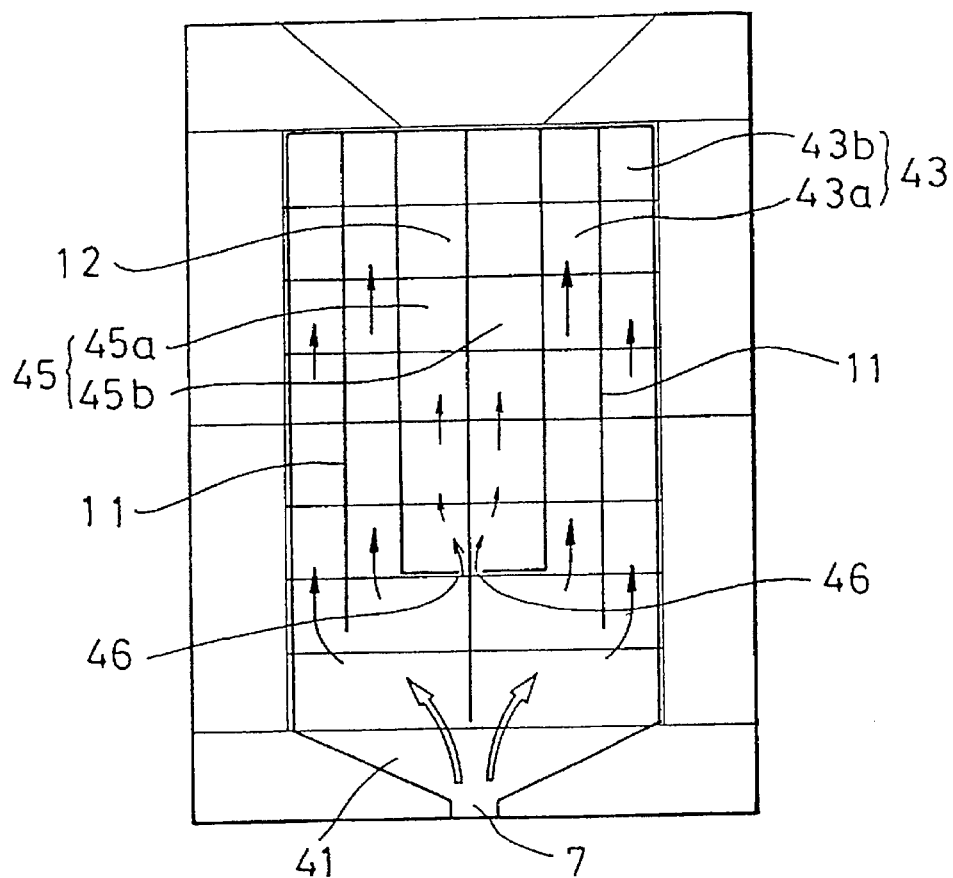
FIG. 27 is a plan view showing an eighth embodiment of the present invention in which one air passage is partitioned.
Figure 28:
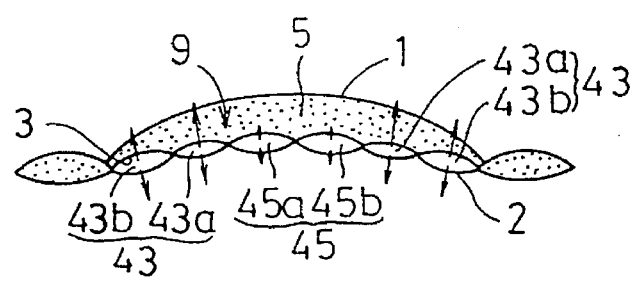
FIG. 28 is a center lateral sectional view of the embodiment shown in FIG. 27.
Figure 29:
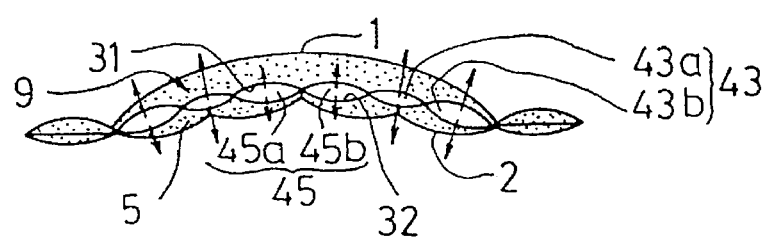
FIG. 29 is a center lateral sectional view showing an embodiment which is similar to the embodiment shown in FIG. 27, but in which an air passage is formed inside the comforter.

In the embodiments as shown in FIGS. 27 to 29, the side air passages 43, 43, which are branched from the foot-part air reservoir 41 communicating with the air opening 7 to both right and left sides, and the center air reservoir 45 are divided into thin-width side air passages 43a, 43b and thin-width center air reservoirs 45a, 45b by joint lines 11, 12. An appropriate quantity of warm air is introduced to the thin-width center air reservoirs 45a, 45b through air-permeable portions 46, 46 formed close to the joint line 12. As a result, the swelling of the air passage is restricted to that of an air passage of small sectional area, so that the swell of the comforter as a whole can be suppressed to a relatively small one.

FIG. 28 shows an embodiment in which the side air passages and the center air reservoir formed in the rear cloth 2 of the comforter are divided into thin-width side air passages 43a, 43b and thin-width center air reservoirs 45a, 45b by joint lines 11, 12. FIG. 29 shows an embodiment in which the side air passages and the center air reservoir formed in the comforter interior are divided into thin-width side air passages 43a, 43b and thin-width center air reservoirs 45a, 45b.

Figure 30:
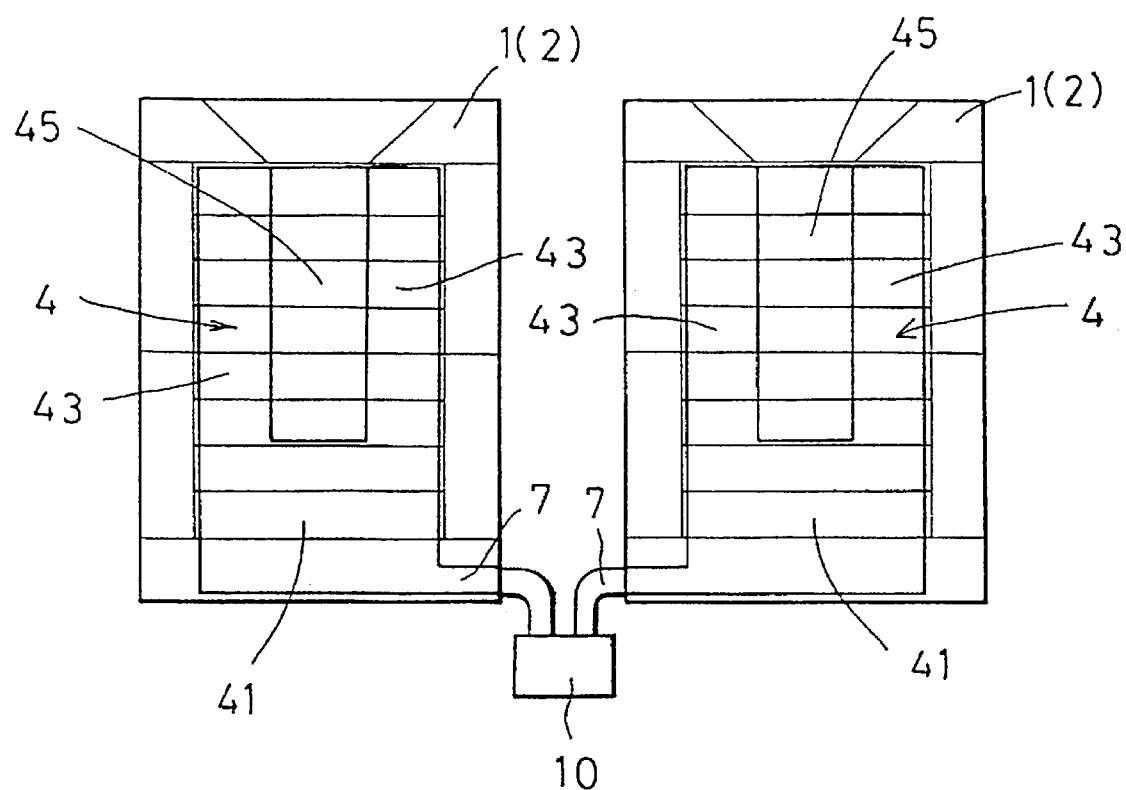
FIG. 30 is a plan view showing an example of the state of use in which air openings to the air passage are provided at right and left side edges of the hem of the comforter, and in which warm air is fed to two sets of comforters by one warm/cool air blower.

The air opening 7 for feeding warm air to the air passages does not necessarily need to be provided in a center of the hem of the comforter. FIG. 30 shows an embodiment in which the air opening 7 is opened on both right and left sides of the hem of the comforter. In this embodiment, paired is a comforter having an air opening opened on the right edge portion and the other comforter having an air opening opened on the left edge portion, and two sets of comforters juxtaposed in series can be fed with warm air from one warm/cool air blower 10.

According to the air controlled comforter of the present invention as described in claim 1, warm or cool air is fed to air passages formed on the rear cloth of the comforter, whereby the sleeping space of the bed is adjusted to a comfortable temperature, and moisture is removed when the fed warm or cool air is discharged into the atmosphere by passing through the comforter. Accordingly, the comforter has an advantage that it creates an ideal sleeping environment of low humidity and appropriate temperature by feeding warm air in winter and cool air (room-temperature air) in summer. Also, the comforter is dried by itself, it is unnecessary to dry the comforter after use, as would be involved conventionally.

According to the present invention as described in claim 3, the air, permeable cloth does not appear outside the comforter, so that the comforter can have a good appearance.

According to the present invention as described in claim 4, warm air is fed to the whole comforter as uniformly as possible. Thus, temperature and humidity can be controlled without irregularities.

According to the present invention as described in claim 4, air fed to the first air passage and the second air passage can be switched over, so that selective control of the air feed conditions can be performed. Thus, an optimum sleeping environment can be obtained promptly immediately before and after the sleeper goes to bed, and a less-stimulative, stable, and indirect air feed conditions can be obtained during sleep.

According to the present invention as described in claim 5 and 6, warm air is fed from the hem or both sides of the sleeper as much as possible, so that the warm air will be less fed to the chest part and the like. Thus, the sleeper will be less stimulated so that a soft, peaceful sleeping environment can be created.

According to the present invention as described in claim 7, the air passage is formed inside the comforter, and warm air is fed to the sleeping space indirectly through a heat insulating material so that the raw air will not be fed to the sleeper. Accordingly, a less-stimulative, stable, and peaceful sleeping environment can be created.

According to the present invention as described in claim 8, fed warm air will never be discharged around the mouth of the sleeper, so that the comforter can be one that will cause the sleeper to become thirsty or stuffy during sleep.

According to the present invention as described in claim 9, the comforter can be freed from such a possibility that the air passage may swell due to fed air and, as a result, the comforter may also swell too much, becoming difficult to use.

What is claimed is:

1. An air controlled comforter comprising a front cloth (1) and a rear cloth (2), and an upper air-permeable cloth (31) and a lower air-permeable cloth (32) arranged between the front cloth and the rear cloth and made from a cloth material having air-permeability, wherein an air passage (4) ranging from a hem to a center part of the comforter is defined by joining together the two air-permeable cloths of the upper air-permeable cloth (31) and the lower air-permeable cloth (32); the front cloth (1) and the rear cloth (2), and the upper air-permeable cloth (31) and the lower air-permeable cloth (32) are joined together at their peripheral edges; a heat insulating material (5) such as feather, wool, and cotton is filled in spaces between the front cloth (1) and the upper air-permeable cloth (31) and between the lower air-permeable cloth (32) and the rear cloth (2); and wherein the air passage (4) formed between the upper air-permeable cloth (31) and the lower air-permeable cloth (32) is opened at the hem of the comforter, where an air opening (7) for feeding warm or cool air is provided at the opening and a means for feeding the warm or cool air into the air opening.

2. An air controlled comforter having a front cloth and a rear cloth joined together at peripheral edges thereof, comprising an upper air-permeable cloth provided between the front cloth and the rear cloth, and joined with the front cloth at a peripheral portion of the upper air-permeable cloth;

a lower air-permeable cloth provided between the upper air-permeable cloth and the rear cloth, and joined with the rear cloth at a peripheral portion of the lower air-permeable cloth; and insulating material contained between the front cloth and the upper air-permeable cloth and between the lower air-permeable cloth and the rear cloth, wherein an air passage is formed between the upper air-permeable cloth and the lower air-permeable cloth;

an air opening is provided at a foot portion of the comforter for feeding a temperature controlled air into the air passage through the air opening;

a means for forcing the temperature controlled air into the air opening.

* * * * *